(12) United States Patent
Nicoll et al.

(10) Patent No.: US 11,571,526 B2
(45) Date of Patent: Feb. 7, 2023

(54) INHALER DEVICE FOR INHALABLE LIQUIDS

(71) Applicant: Medical Developments International Limited, Scoresby (AU)

(72) Inventors: Kenneth Andrew Nicoll, Scoresby (AU); Mathew James Dickson, Mulgrave (AU)

(73) Assignee: MEDICAL DEVELOPMENTS INTERNATIONAL LIMITED, Scoresby (AU)

( * ) Notice: Subject to any disclaimer, the term of this patent is extended or adjusted under 35 U.S.C. 154(b) by 549 days.

(21) Appl. No.: 16/330,897

(22) PCT Filed: Sep. 6, 2017

(86) PCT No.: PCT/AU2017/050965
§ 371 (c)(1),
(2) Date: Mar. 6, 2019

(87) PCT Pub. No.: WO2018/045418
PCT Pub. Date: Mar. 15, 2018

(65) Prior Publication Data
US 2019/0209792 A1    Jul. 11, 2019

(30) Foreign Application Priority Data
Sep. 6, 2016 (AU) .............................. 2016903579

(51) Int. Cl.
*A61M 15/00*    (2006.01)
*A61M 11/04*    (2006.01)
(Continued)

(52) U.S. Cl.
CPC ........ *A61M 15/0016* (2014.02); *A61M 11/04* (2013.01); *A61M 15/00* (2013.01);
(Continued)

(58) Field of Classification Search
CPC ... A24F 42/20; A61M 15/06; A61M 16/0016; A61M 16/0018; A61M 16/01; A61M 16/14; B65D 51/2835
See application file for complete search history.

(56) References Cited

U.S. PATENT DOCUMENTS

| | | | | |
|---|---|---|---|---|
| 957,548 A | * | 5/1910 | Doane | A61M 15/00 128/203.24 |
| 3,521,643 A | * | 7/1970 | Toth | A61M 15/06 128/202.21 |

(Continued)

FOREIGN PATENT DOCUMENTS

| | | | | |
|---|---|---|---|---|
| FR | 2654002 A1 | * | 5/1991 | ............. A24F 42/20 |
| WO | WO1997/003711 A2 | | 2/1997 | |

(Continued)

OTHER PUBLICATIONS

Penthrox Datasheet and training pack NPL (Year: 2009).*
(Continued)

*Primary Examiner* — Kathryn E Ditmer
(74) *Attorney, Agent, or Firm* — Westman, Champlin & Koehler, P.A.

(57) ABSTRACT

The present invention provides a new inhaler device for the administration of inhalable liquids to a patient offering one or more advantages or improvements over known inhalers, particularly inhalers for the delivery of halogenated volatile liquids such as methoxyflurane for use as an analgesic.

31 Claims, 9 Drawing Sheets

(51) Int. Cl.
*A61M 16/01* (2006.01)
*A61M 16/14* (2006.01)
*A61M 16/00* (2006.01)

(52) U.S. Cl.
CPC ..... *A61M 15/0018* (2014.02); *A61M 16/0093* (2014.02); *A61M 16/01* (2013.01); *A61M 16/14* (2013.01); *A61M 2202/048* (2013.01)

(56) References Cited

U.S. PATENT DOCUMENTS

| | | | | |
|---|---|---|---|---|
| 4,011,864 | A * | 3/1977 | Guichard | A61M 15/009 128/200.23 |
| 4,369,798 | A * | 1/1983 | Jackson | A24F 13/02 131/187 |
| 4,657,032 | A * | 4/1987 | Dorr | A24D 1/002 131/336 |
| 4,725,442 | A | 2/1988 | Haynes | |
| 4,756,318 | A * | 7/1988 | Clearman | A24D 1/22 131/359 |
| 6,039,198 | A * | 3/2000 | Wolfe | B65D 51/223 215/228 |
| 6,345,625 | B1 * | 2/2002 | Chew | A24D 3/04 131/187 |
| 2004/0255951 | A1 * | 12/2004 | Grey | A61M 16/04 128/207.14 |
| 2006/0191546 | A1 * | 8/2006 | Takano | A24F 42/20 131/270 |
| 2007/0283971 | A1 * | 12/2007 | Gidding | A24F 13/00 131/202 |
| 2008/0230077 | A1 * | 9/2008 | Martilik | A24F 13/00 131/202 |
| 2010/0083963 | A1 * | 4/2010 | Wharton | A61M 11/002 128/203.15 |
| 2011/0240047 | A1 * | 10/2011 | Adamic | A24F 3/00 131/328 |
| 2011/0297166 | A1 * | 12/2011 | Takeuchi | A24F 42/60 131/274 |
| 2012/0111346 | A1 * | 5/2012 | Rinker | A24F 42/10 131/328 |
| 2013/0160780 | A1 * | 6/2013 | Matsumoto | A24F 42/60 131/329 |
| 2014/0060531 | A1 * | 3/2014 | Brambilla | A61M 15/0065 128/203.12 |
| 2015/0150305 | A1 | 6/2015 | Shenkal | |
| 2016/0219932 | A1 * | 8/2016 | Glaser | A24F 40/485 |
| 2016/0270446 | A1 * | 9/2016 | Shenkal | B01D 46/0026 |
| 2017/0181472 | A1 * | 6/2017 | Batista | A24F 40/70 |

FOREIGN PATENT DOCUMENTS

| | | | |
|---|---|---|---|
| WO | WO1999/034762 | A1 | 7/1999 |
| WO | WO2002/022195 | A2 | 3/2002 |
| WO | WO2003/032890 | A1 | 4/2003 |
| WO | WO2007/033400 | A1 | 3/2007 |
| WO | WO2008/036858 | A2 | 3/2008 |
| WO | WO2008/040062 | A1 | 4/2008 |
| WO | WO2008/070490 | A2 | 6/2008 |
| WO | WO2009/094459 | A1 | 7/2009 |
| WO | WO2009/094460 | A2 | 7/2009 |
| WO | WO2009/117529 | A2 | 9/2009 |
| WO | WO2010/017586 | A1 | 2/2010 |
| WO | WO-2010017586 | A1 * | 2/2010 ........ A61M 16/1065 |
| WO | WO2010/025505 | A1 | 3/2010 |
| WO | WO2010/129686 | A1 | 11/2010 |
| WO | WO2010/129796 | A1 | 11/2010 |
| WO | WO2010/135436 | A1 | 11/2010 |
| WO | WO2012/116187 | A1 | 8/2012 |
| WO | WO2013/016511 | A1 | 1/2013 |
| WO | WO2013/106608 | A1 | 7/2013 |
| WO | WO2013/149263 | A1 | 10/2013 |
| WO | WO2014/143964 | A2 | 9/2014 |
| WO | WO2015/034978 | A1 | 3/2015 |
| WO | WO2017/011865 | A1 | 1/2017 |
| WO | WO2017/011866 | A1 | 1/2017 |
| WO | WO2017/011867 | A1 | 1/2017 |
| WO | WO2017/011868 | A1 | 1/2017 |

OTHER PUBLICATIONS

International Search Report and Written Opinion for corresponding international application No. PCT/AU2017/050965, dated Oct. 19, 2017.
Terrell, R.C. Anesthesiology (2008) 108 (3): 531-3 (3 pages).
Robbins, B.H., "Preliminary studies of the anesthetic activity of fluorinated hydrocarbons", J Pharmacol Exp Ther, Feb. 1946; 86: pp. 197-204.

* cited by examiner

INHALER DEVICE FOR INHALABLE LIQUIDS

CROSS-REFERENCE TO RELATED APPLICATION(S)

This Application is a Section 371 National Stage Application of International Application No. PCT/AU2017/050965, filed Sep. 6, 2017, and published as WO/2018/045418 on Mar. 15, 2018, in English, which claims priority to Australian patent application 2016903579, filed Sep. 6, 2016, in English, the contents of which are each hereby incorporated by reference in their entirety.

FIELD

The present invention relates to an inhaler device for inhalable liquids, in particular for the administration of inhalable volatile liquids such as halogenated volatile liquids, to a patient.

BACKGROUND

The storage and administration of inhalable liquids to patients that comprise active agents, or that are themselves the active agent, commonly presents challenges. Due to patient preference and ease of self-administration or administration in a hospital setting or other settings as required, active agents such as therapeutic agents or pharmaceutical agents, are often formulated for oral delivery in the form of tablets and capsules, nasal delivery in the form of sprays and liquid formulations for intravenous delivery.

Where it is advantageous to administer active agents to a patient's lungs, for example to treat or alleviate respiratory diseases, the active agent may be administered by the oral inhalation route, alone or in combination with the intranasal route. Suitable inhaler devices may include, for example, metered dose inhalers and dry powder inhalers. These types of oral inhalation devices typically require pressurised means to deliver the active agent to the desired site of action in the lungs. In addition, liquids that contain active agents or that are themselves the active agent usually require transformation into an inhalable, respirational, form at the point of administration to be suitable for delivery by the inhalation route. Transforming a liquid into an inhalable form, such as by nebulisation or aerosolizing into respirational sized droplets or heating to form a vapor, requires delivery devices to include moving, mechanical, heating and/or electrical means which adds to the complexity of the design, manufacturing and end user costs, operability and/or patient use.

The use of volatile liquids as active agents or comprising active agents is known. One such example is halogenated volatile liquids. Halogenated volatile liquids have been described as useful for inducing and/or maintaining anaesthesia (including amnesia, muscle paralysis, and/or sedation) and/or analgesia and may therefore be useful as anaesthetics and/or analgesics. The anaesthetic properties of fluorinated compounds have been known since at least 1946 (Robbins, B. H. *J Pharmacol Exp Ther* (1946) 86: 197-204). This was followed by the introduction of fluoroxene, halothane and methoxyflurane into clinical use in the 1950s and the subsequent development of enflurane, isoflurane, sevoflurane and desflurane which are in clinical use in some countries today (Terrell, R. C. *Anesthesiology* (2008) 108 (3): 531-3).

Halogenated volatile liquids, when used for general anaesthesia, may be delivered to a patient under positive pressure via a delivery system that includes a vaporizer and a flow of breathable carrier gas. More recently, halogenated volatile liquids have been formulated for use in local or regional anaesthesia and delivery via non-inhalation routes. Examples include formulation as: microdroplets for intradermal or intravenous injection (e.g. U.S. Pat. No. 4,725,442); aqueous solutions for intrathecal or epidural delivery (e.g. WO2008/036858); swab, droplets, spray or aerosol for transmucosal delivery (e.g. WO2010/025505); aqueous based solutions comprising an extractive solvent in an amount effective to reduce the volatility, vaporisation or evaporation of the volatile anaesthetic for transdermal, topical, mucosal, buccal, rectal, vaginal, intramuscular, subcutaneous, perineural infiltration, intrathecal or epidural delivery (e.g. WO2009/094460, WO2009/094459); compositions suitable for formulation into a medical patch (e.g. WO2014/143964); compositions suitable for formulation as a solution, suspension, cream, paste, oil, lotion, gel, foam, hydrogel, ointment, liposome, emulsion, liquid crystal emulsion and nanoemulsions for topical, intrathecal, epidural, transdermal, topical, oral, intra-articular, mucosal, buccal, rectal, vaginal, intramuscular, intravesical and subcutaneous delivery (e.g. WO2008/070490, WO2009/094460, WO2010/129686); and stable and injectable liquid formulations (WO2013/016511).

The main consideration(s) for the safe storage and handling of volatile liquids commonly include vapor pressure build up, the robustness of the container and the integrity of the container seal(s). The chemical nature of the volatile liquid may also be important if the active agent is capable of permeating, solubilizing or otherwise reacting with the container material(s) upon storage. A number of storage containers for halogenated volatile liquids have been described including: rigid polymeric containers as a replacement for glass vials, such as capped bottles large tanks, shipping containers (e.g. WO1999/034762, WO2012/116187); rigid polymeric bottles fitted with a gasketless valve assembly and pliable containers with a threaded spout for fluid connection to deliver liquid anaesthetics to an anaesthetic machine or vaporizer (e.g. WO2010/135436, WO2013/106608, WO2013/149263, WO2015/034978); a container with a capped membrane for delivering a stored liquid anaesthetic to a vaporizer via a slotted tube (WO2009/117529); and rigid polymeric and aluminium containers optionally coated with materials to impart or enhance vapor barrier characteristics or container inertness (e.g. WO2002/022195, WO2003/032890, WO2010/129796).

Despite the various advances in formulating volatile liquids in non-inhalable forms, such as the halogenated volatile liquids, as well as containers to store them, there still remains a need for inhalable forms of volatile liquids and devices to store and/or administer them to patients.

Attempts to design new inhalers for inhalable medicines in general are ongoing. For example, WO2008/040062 describes a diverse number of inhaler device concepts that depend on complex constructions and moving parts for storing and/or delivering inhalable liquids and powdered solids into a user's mouth or nose. The various devices described are adapted to hold one or two medicament containers in the form of pressurised canisters, ampoules, vials and plungers. The devices are described as being activated by sliding an outer wall of the device in relation to an inner wall of the device to deliver the liquid medication from a medication container. In a number of embodiments, the device includes a moveable mouthpiece which deploys in order to open the air pathway. The device is also described as including one or more one-way valves to provide a unidirectional air flow for one or both inhaled air and exhaled air (a series of one-way valves to direct the flow of inhaled and exhaled air has also been generally described in WO2007/033400 which is an incorporation by reference of the device described in WO1997/003711).

When required for use, the devices of WO2008/040062 are claimed as being capable of releasing the medication by punching means namely two punches to perforate the two frangible ends respectively of a medication container having frangible ends, although various other means are generally described including: pressurised means (e.g. by a pressurised canister); frangible means (e.g. by rupturing an ampoule with a striker or by punching a frangible membrane or seal of a vial with punch means); crushable means (e.g. by crushing a vial with a plunger); dislodging means (e.g. by dislodging an unscrewed cap from a vial); and plunging means (e.g. by plunging the medication from the plunger barrel).

However, inhalable liquids such as halogenated volatile liquids require an effective air chamber into which the vapor may evaporate and allow an effective airflow through the air/vapor chamber for delivery to a patient. Accordingly, embodiments such as those described in, for example, FIGS. 48A, 48B, 48C, 49A, 49B, 50A, 50B, 51A, 51B, 56A, 56B, 57, 58A, 58B, 58C and 58D of WO2008/040062, would not be expected to work in practice as the evaporative means (or wick) is prevented from being effectively exposed to the released liquid by the walls of the liquid storage container itself.

The present invention provides a new inhaler device for the administration of inhalable liquids to a patient offering one or more advantages or improvements over known inhalers, particularly inhalers for the delivery of halogenated volatile liquids such as methoxyflurane for use as an analgesic.

SUMMARY

According to an aspect of the invention there is provided an inhaler device for the delivery of an inhalable liquid to a patient, said device comprising:
(1) A base end;
(2) A mouthpiece end; and
(3) A co-axial air inhale-exhale chamber arrangement comprising:
  (a) an air inhale chamber comprising a liquid inlet hole and a passive evaporation support material for receiving the inhalable liquid from a liquid storage container and delivering to the patient as a vapor upon inhalation by the patient through the mouthpiece end; and
  (b) an air exhale chamber comprising an air filtering means to filter the vapor upon exhalation by the patient through the mouthpiece end and exit through the base end;
wherein the air exhale chamber is co-axially positioned internally within the air inhale chamber.

In an alternative embodiment, the air inhale chamber is co-axially positioned internally within the air exhale chamber.

In one embodiment the co-axial air inhale-exhale chamber arrangement comprises a connector to co-axially position the air exhale chamber internally within the air inhale chamber or vice versa.

In one embodiment, the mouthpiece end comprises a mouthpiece chamber wherein the vapor is inhaled into the mouthpiece chamber from the air inhale chamber and exhaled into the mouthpiece chamber and exited through the base end via the air exhale chamber.

In one embodiment the device may further comprise a multi-directional valve arrangement (such as a two-way valve) and/or one or more one-way valves.

In one embodiment, the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In a preferred embodiment, the inhalable liquid is methoxyflurane for use as an analgesic.

DETAILED DESCRIPTION

Figure 1:
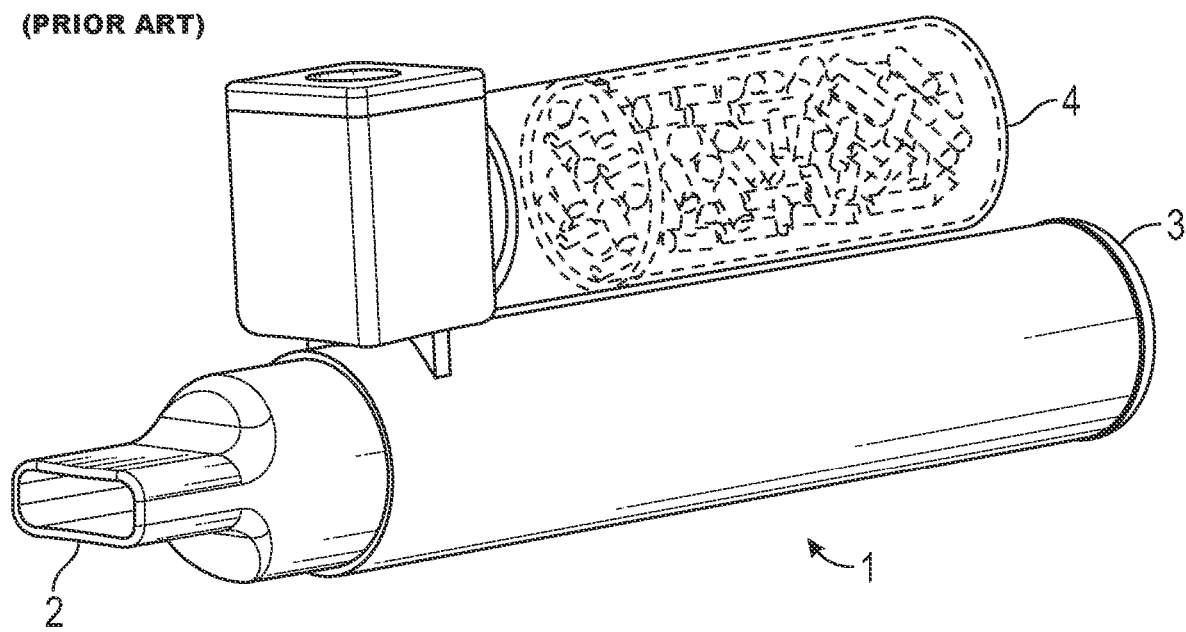
FIG. 1 shows a prior art inhaler device, referred to as the Green Whistle™ inhaler device (Medical Developments International Limited) that is currently used to administer methoxyflurane.

Inhaler devices that are useful for administering inhalable liquids may be generally considered to operate by either passive or active means in order to deliver the active agent(s)

to a patient. Inhaler devices with active means may include pressurized, moving, mechanical, heating and/or electrical means to, for example, nebulise, vaporize and/or generally deliver the active agent(s). In contrast, inhaler devices with passive means rely solely on the vaporisation or evaporation of the active agent(s) at ambient conditions and respiration of the patient to deliver the active agent(s).

The Analgizer™ inhaler device (Abbott Laboratories Corporation) is an example of a device that operates by passive means to deliver an inhalable liquid. According to the USPTO TESS database, the Analgizer™ was a registered, now lapsed, trademark in respect of an inhaler for the supervised self-administration of inhalation anaesthesia and was first used in 1968. The Analgizer™ was a very simple device that consisted of a white cylindrical polyethylene open-ended tube having a mouthpiece and an absorbent wick of polypropylene which was tightly rolled into a 'Swiss-roll' shape, i.e. cross-sectional view. The inhalation anaesthetic, methoxyflurane (15 mL), was poured into the open ended base of the inhaler and onto the tightly wound wick, just prior to use. A patient was then able to self-administer the liquid anaesthetic by inhaling through the mouthpiece.

The Green Whistle™ inhaler device (Medical Developments International Limited) was subsequently developed during the 1990s and has since been used in Australia for the delivery of Penthrox®/™ (methoxyflurane) as an analgesic (1.5 mL or 3 mL, storage brown glass vial container with screw cap). Although similar in its simplicity of design to the Analgizer™, the Green Whistle™ device includes certain functional improvements such as the inclusion of a one-way valve at the base end to prevent drug vapor loss from the device upon patient exhalation and an activated carbon ('AC') chamber designed to be externally fit into a dilution hole in the mouth piece to filter exhaled drug vapors. Additional design modifications to the base end included the introduction of cap lugs to assist removal of the cap from the glass vial used to store the drug dose to be delivered, a dome to facilitate the spread of the poured liquid onto the 'S-shaped' wick (i.e. cross-sectional view) or, in the alternative to a dome, an inlet nipple to allow for the attachment of a breathable gas line to direct the gas through the device. The Green Whistle™ device is designed for single patient use.

Methoxyflurane (Penthrox®/™, Medical Developments International Limited) offers a non-narcotic, i.e. non-opioid analgesic alternative to common analgesics such as morphine and fentanyl. Methoxyflurane also presents an alternative to analgesics which are administered in oral tablet form or intravenously to a patient and may therefore be particularly useful when rapid pain relief is required in clinical, surgical (e.g. pre- and post-operative) and/or emergency settings (e.g. emergency department and triage management as well as by first-responders such as paramedics and search and rescue teams). However, the Green Whistle™ device is currently the only device that is commercially available to administer methoxyflurane. According to the device's instructions for use, the administrator is required to hold the methoxyflurane bottle upright to use the base of the inhaler to loosen the bottle cap and then to remove the cap by hand before tilting the inhaler to a 45° angle and pouring the contents of the bottle into the base while rotating the device. An AC-chamber may be optionally fitted externally to the device either beforehand or afterwards. While the device is effective, the number of steps and separate components may present handling difficulties for the administrator or self-administrator, for example, in high-stress and/or emergency settings.

The evaporative means within the Analgizer™ and Green Whistle™ devices essentially extends longitudinally throughout their entire device length. Further, those devices do not accommodate an internally co-axially located air exit chamber comprising air filtering means, such as activated carbon (AC) granules.

The present invention provides a new inhaler device for the administration of inhalable liquids to a patient, such as halogenated volatile liquids, particularly methoxyflurane for use as an analgesic, the device having one or more advantages or improvements over known inhalers.

Definitions

Unless otherwise herein defined, the following terms will be understood to have the general meanings which follow.

'Active agent' refers to therapeutic agents and non-therapeutic agents and compounds, formulations and compositions comprising them.

'Alleviate', 'Alleviation' and variations thereof refers to relieving, lessening, reducing, ameliorating or an improvement in the symptom(s) and/or underlying cause(s) of a condition and/or disease in a patient.

'Delivery dose' refers to the dose of inhalable liquid or active agent for administration to a patient.

'Filter', 'Filtering' and variations thereof refers to the ability of a substance to absorb, adsorb, capture, trap, scavenge, scrub or partially or entirely remove the inhalable volatile liquid vapor from the exhaled breath of a patient upon exhalation.

'Halogenated volatile liquids' refers to volatile liquids which (i) comprise at least one halogen atom selected from the group consisting of a chlorine (Cl), bromine (Br), fluorine (F) and iodine (I) atoms, or (ii) comprise an active agent which comprises at least one halogen atom selected from the group consisting of a chlorine (Cl), bromine (Br), fluorine (F) and iodine (I) atoms. In some embodiments, halogenated, particularly fluorinated, hydrocarbons and halogenated, particularly fluorinated, ethers may be preferred. In some embodiments, halogenated ethers may be particularly preferred and include but are not limited to, halothane (2-bromo-2-chloro-1,1,1-trifluoroethane), sevoflurane (fluoromethyl-2,2,2-trifluoro-1-(trifluromethyl) ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1, 2-trifluoroethyldifluoromethyl ether) and methoxyflurane (2,2-dichloro-1,1-difluoroethylmethyl ether).

'Inhalable liquid' refers to liquids that comprise active agents or that are themselves the active agent and that are readily inhalable or capable of being or adapted to be inhaled by a patient. In some embodiments, inhalable volatile liquids, particularly halogenated volatile liquids are preferred.

'Inhalation', 'Inhalable' and variations thereof refers to the intake of, for example but not limited to air, breathable gases, inhalable liquids, by a patient and includes both oral and nasal inhalation. In some embodiments, oral inhalation is particularly preferred.

'Patient' refers to both human and veterinary patients. In some embodiments, human patients may be particularly preferred. Reference to a patient will therefore be understood to mean the person or animal to whom the inhalable liquid is administered to and in the case of human patients, will be understood to include administration by self-administration.

'Pharmaceutical agent' refers to a drug, or a compound, formulation or composition that comprises a drug, for the treatment of symptom(s) and/or underlying cause(s) of a condition and/or disease in a patient. The term pharmaceutical agent may be used interchangeably with therapeutic agent or active agent.

'Respiratory', 'Respirational' and variations thereof refers to the act of respiring, breathing, inhaling and exhaling, such as for example but not limited to air, breathable gases, inhalable liquids and active ingredients, by a patient.

'Room temperature' refers to ambient temperatures which may be, for example, between 10° C. to 40° C. but more typically between 15° C. to 30° C.

'Therapeutic agent' refers to an active agent, or a compound, formulation or composition (including biological compounds, formulations and compositions) that comprises an active agent, that is capable of treating a patient or offers a therapeutic or medical benefit to a patient or that has or that requires regulatory and/or marketing approval for therapeutic use in a patient. Therapeutic agents include pharmaceutical agents. In contrast, a 'Non-therapeutic agent' will be understood to mean an active agent which may not have or require regulatory and/or marketing approval for a therapeutic use such as, for example, smokeless tobacco products and electronic cigarettes, or does not have a recognised or identified therapeutic use but may be used by a patient for a non-therapeutic reason such as general health, wellbeing or physiological benefit such as, for example, nutraceutical products.

'Treat', 'Treatment' and variations thereof refers to the alleviation, modulation, regulation or halting of the symptom(s) and/or underlying cause(s) of a condition and/or disease in a patient. In some embodiments treatment may include preventative or prophylactic treatment.

'Volatile liquids' refers to substances that predominantly exist in a liquid form but readily form vapors, evaporate or vaporize such that they partially exist in a vapor form under ambient conditions for example, at room temperature and at normal atmospheric pressures.

EMBODIMENTS

Embodiments will now be described with reference to the non-limiting examples.

There is provided an inhaler device for the delivery of an inhalable liquid to a patient, said device comprising:
(1) A base end;
(2) A mouthpiece end; and
(3) A co-axial air inhale-exhale chamber arrangement comprising:
  (a) an air inhale chamber comprising a liquid inlet hole and a passive evaporation support material for receiving the inhalable liquid from a liquid storage container and delivering to the patient as a vapor upon inhalation by the patient through the mouthpiece end; and (b) an air exhale chamber comprising an air filtering means to filter the vapor upon exhalation by the patient through the mouthpiece end and exit through the base end;

wherein the air exhale chamber is co-axially positioned internally within the air inhale chamber.

In an alternative embodiment, the air inhale chamber is co-axially positioned internally within the air exhale chamber.

In one embodiment, the mouthpiece end comprises a mouthpiece chamber wherein the vapor is inhaled into the mouthpiece chamber from the air inhale chamber and exhaled into the mouthpiece chamber and exited through the base end via the air exhale chamber.

To aid the direction of the flow of the air/vapor mixture through the device, more particularly through the co-axial air inhale-exhale chamber arrangement, the device (and more particularly the co-axial air inhale-exhale chamber arrangement), may further comprise a multi-directional valve arrangement (such as a two-way valve) and/or one or more one-way valves.

Accordingly in one embodiment the co-axial air inhale-exhale chamber arrangement comprises a valve.

In one embodiment the device comprises a multidirectional valve located between the mouthpiece chamber and the co-axial air inhale-exhale chamber arrangement whereupon respiration by a patient through the mouthpiece end:

(a) upon inhalation by the patient, opens the multidirectional valve between the air inhale chamber and the mouthpiece chamber to deliver the evaporated liquid in the form of a vapor to the patient and closes the multidirectional valve between the air exhale chamber and the mouthpiece chamber; and (b) upon exhalation by the patient, closes the multidirectional valve between the air inhale chamber and the mouthpiece chamber and opens the multidirectional valve between the air exhale chamber and the mouthpiece chamber to exhaust the expired air through the air filtering means and exit out of the base end.

In one embodiment the multidirectional valve is a two-way valve.

In another embodiment the device comprises a one-way valve located between the mouthpiece chamber and the air inhale chamber whereupon inhalation by the patient, opens the one-way valve between the air inhale chamber and the mouthpiece chamber to deliver the evaporated liquid in the form of a vapor to the patient.

In another embodiment the device comprises a one-way valve located between the mouthpiece chamber and the air exhale chamber whereupon exhalation by the patient, opens the one-way valve between the air exhale chamber and the mouthpiece chamber to exhaust the expired air through the air filtering means and exit out of the base end.

In one embodiment the device comprises a one-way valve located at the base end of the air exhale chamber whereupon exhalation by the patient, opens the one-way valve to exhaust the expired air from the base end.

In one embodiment there is provided a one-way valve located between the mouthpiece chamber and the air exhale chamber and a one-way valve positioned between the mouthpiece chamber and the air exhale chamber whereupon respiration by a patient through the mouthpiece end:

(a) upon inhalation by the patient, opens the one-way valve between the air inhale chamber and the mouthpiece chamber to deliver the evaporated liquid in the form of a vapor to the patient and closes the one-way valve between the air exhale chamber and the mouthpiece chamber; and (b) upon exhalation by the patient, closes the one-way valve between the air inhale chamber and the mouthpiece chamber and opens the one-way valve between the air exhale chamber and the mouthpiece chamber to exhaust the expired air through the air filtering means and exit out of the base end.

In one embodiment, the base end, the mouthpiece end comprising a mouthpiece chamber and the co-axial air inhale-exhale chamber arrangement are integrally formed features of the inhaler device. In another embodiment the base end, the mouthpiece end comprising a mouthpiece chamber and the co-axial air inhale-exhale chamber arrangement are separately formed features of the inhaler device and adapted to be assembled for use.

In a further embodiment the air inhale chamber and air exhale chamber are integrally formed features of the co-axial air inhale-exhale chamber arrangement. In yet another embodiment the air inhale chamber and air exhale chamber are separately formed features of the inhaler device and adapted to be assembled for use.

In one embodiment the co-axial air inhale-exhale chamber arrangement comprises a connector to co-axially position the air exhale chamber internally within the air inhale chamber or vice versa.

In one embodiment the connector is integrally formed with the air inhale and air exhale chambers.

In an alternative embodiment the connector comprises a first connector component adapted to join with a second connector component wherein the air inhale chamber comprises said first connector component and the air exhale chamber comprises the second connector component. In one embodiment the connector is a snap-fit joint. In one embodiment the first connector component is adapted to join by slideably connecting with the second connector component.

In one embodiment the connector is a keyway connector. In one embodiment the connector is a male-female connector. In one embodiment the connector is a tongue and groove connector. In one embodiment the first connector component and the second connector component may be independently selected from the group consisting of a key way connector component, a tongue connector component, a groove connector component, a male connector component and a female connector component.

While a connector may aid in the co-axial positioning of the air exhale chamber internally within the air inhale chamber, the air exhale chamber may also be co-axially positioned internally within the air inhale chamber by virtue of the passive evaporative support material which may partially or completely surround the external surface of the air exhale chamber. In one embodiment the passive evaporative support material may optionally be positioned in the air inhale chamber by a support means as further described herein. Accordingly, in one embodiment the connector is absent.

The air inhale chamber comprises a liquid inlet hole and a passive evaporation support material to receive the liquid from a liquid storage container and release it as a vapor by passive evaporation from the exposed surface of the passive evaporation support material into the air inhale chamber for delivery to a patient upon inhalation.

The liquid may be deposited from the liquid storage container onto the passive evaporation support material as further described herein.

It may also be desirable to direct the site(s) of deposition of the liquid onto the passive evaporation support material and to improve its distribution once deposited by use of an optional inlet guide. In one embodiment, the liquid inlet hole comprises an optional liquid inlet guide. The inlet guide may be in the form of a funnel, gutter, channel, chute or the like. In one embodiment the inlet guide is selected from the group consisting of a funnel, a gutter, a channel and a chute. Without wishing to be bound by theory, the inlet guide may offer the advantage of assisting the distribution of the poured liquid onto and throughout the passive evaporation support material by being designed to disrupt or break the surface tension of the poured liquid as it leaves the inlet guide and/or direct the location of the liquid's initial site(s) of contact with the passive evaporation support material.

It may also be desirable to minimise or prevent the liquid from entering into the mouthpiece chamber by directing the site(s) of deposition of the liquid onto the passive evaporation support material and to improve its distribution once deposited by use of an optional liquid guide within the air inhale chamber. In one embodiment, the air inhale chamber may comprise an optional liquid guide. The optional liquid guide may comprise any suitable arrangement to guide the liquid (for example in an axial direction) onto the passive evaporation support material while still allowing the air/vapor mixture to pass through the air inhale chamber (for example in a radial direction) and into the mouthpiece chamber upon inhalation by the patient. In one embodiment the device comprises a liquid guide to direct the delivered liquid in the air inhale chamber to make contact with the passive evaporation support material. In one embodiment the liquid guide is selected from the group consisting of a baffle arrangement, a castellation arrangement, a radial arrangement of guides and alternating air gaps, a mesh arrangement of air gaps and guide fingers and combinations thereof.

The passive evaporation support material may be made from any material that is suitable for absorbing the inhalable liquid and passively releasing it as a vapor. Materials which have wicking properties are particularly preferred passive evaporation support material for use in the present device. Wicking properties will generally be understood to include the ability of a material to facilitate or enhance the rate of evaporation or vaporisation of a liquid from its surface by distributing the liquid, whether by drawing, spreading, pulling or otherwise, throughout the material from its initial point of contact and/or as it evaporates from an exposed surface area of the material. Accordingly, in one embodiment the passive evaporation support material is a wicking material. In one embodiment the wicking material is a wicking felt or a porous polymeric material. In a preferred embodiment the wicking material is a polypropylene wicking felt.

The passive evaporative support material may be positioned within the air inhale chamber such that it partially or completely surrounds the external surface of the air exhale chamber. In one embodiment the passive evaporative support material may be positioned in the air inhale chamber by a support means. The support means may assist with positioning of the passive evaporative support material by holding it in place to prevent or reduce movement.

The support means may also create an air gap between a surface of the passive evaporative support material and an internal surface of the air inhale chamber. The support means may therefore be designed to enable the air/vapor mixture to pass through the air inhale chamber above and/or below the passive evaporative support material which increases, for example doubles, the surface area of the passive evaporative support material that is exposed to a flow of air across its surface to deliver the evaporated liquid in the form of a vapor when the patient inhales.

In one embodiment the device comprises a support means adapted to create an air gap between a surface of the passive evaporative support material and an internal surface of the air inhale chamber. In one embodiment the support means comprises one or more ridges or ribs that run longitudinally along a length of an internal surface of the air inhale chamber. In one embodiment the passive evaporative support material is positioned within the air inhale chamber between two or more ridges or ribs that run longitudinally along a length of an internal surface of the air inhale chamber. In one embodiment the support means is adapted to expose one surface area of the passive evaporative support material to a flow of inhaled air. In another embodiment the support means is adapted to expose two surface areas of the passive evaporative support material to a flow of inhaled air.

In another embodiment the passive evaporation support material comprises two or more ridges or ribs adapted to run longitudinally along a length of an internal surface of the air inhale chamber when the passive evaporative support material is positioned in the air inhale chamber to expose one or two surface areas of the passive evaporative support material to a flow of inhaled air.

The device may optionally comprise an exhaust port to prevent or reduce mixing of the exhaled breath from the patient as it exits the air exhale chamber out of the base end of the device with the intake flow of air into the air inhale chamber from the base end when the patient inhales. In one embodiment the air exhale chamber comprises an exhaust port.

It may be considered desirable to filter the exhaled air which contains a proportion of the inhaled vapor in order to reduce the exposure of others in close proximity to the patient during administration. The Green Whistle™ inhaler device of the prior art includes an activated carbon ('AC') chamber component that is separately manufactured and designed to be externally fit into a dilution hole in the mouth piece to filter exhaled drug vapors.

In contrast to the Green Whistle™ inhaler device, the present device provides an internally positioned air exhale chamber that comprises an air filtering means to filter the vapor upon exhalation by the patient in a co-axial air inhale-exhale chamber arrangement.

Examples of an air filtering means include but are not limited to one or more air filtering substances such as activated carbon ('AC'), preferably in granular form. In one embodiment the air filtering means comprises activated carbon ('AC'), preferably in a granular form. In one embodiment the air exhale chamber is adapted to internally receive activated carbon granules. In a further embodiment the activated carbon granules are present within the air exhale chamber. In another embodiment the air filtering means is a cartridge comprising an air filtering substance such as activated carbon ('AC'), preferably in granular form and/or one or more filters such as optimised filter paper(s). The cartridge may be insertably removable from the air exhale chamber or may be integrally formed therein. In one embodiment the cartridge comprising the air filtering substance(s) is insertably removable from the air exhale chamber by for example, a sliding guide means in the air exhale chamber wall(s). In another embodiment, the cartridge comprising the air filtering substance(s) is integrally formed with the air exhale chamber wall(s).

Activated carbon ('AC'), including in a granular form as described herein, may also comprise carbon dust. It may therefore also be considered desirable to prevent exposure of the patient and others in close proximity to the patient to carbon dust. In one embodiment the air exhale chamber comprises activated carbon ('AC') and a carbon dust retaining filter. In one embodiment the carbon dust retaining filter is positioned in the base end of the device. In one embodiment the carbon dust retaining filter comprises a polyester mesh material.

The device may generally adopt the same external cross-sectional shape along its length. In one embodiment the cross-sectional shape of the device is selected from the group consisting of circular, semi-circular, elliptical, semi-elliptical, oval, ovoidal, square, rectangular, trapezoidal, triangular and combinations thereof. Shapes having square corners may also be replaced with rounded corners, for example, a rectangle having a square corner replaced by a rounded one may be referred to as a rounded rectangular shape.

In one embodiment the cross-sectional shape of the device is selected from cylindrical, rectangular, rounded rectangular, trapezoidal and rounded trapezoidal. In one embodiment the cross-sectional shape of the device is cylindrical. In one embodiment the cross-sectional shape of the device is rounded rectangular.

In a further embodiment, the cross-sectional shape may taper along its length from the base end to the mouthpiece end or vice versa. In one embodiment the cross-sectional shape tapers from the base end towards the mouthpiece end.

The cross-sectional shape of the air inhale chamber and air exhale chamber may be the same or different. In one embodiment the cross-sectional shape of the air inhale chamber and the air exhale chamber are the same. In one embodiment the cross-sectional shape of the air inhale chamber and the air exhale chamber are different.

In one embodiment cross-sectional shape of the air inhale chamber and cross-sectional shape of the air exhale chamber are independently selected from the group consisting of circular, semi-circular, elliptical, semi-elliptical, oval, ovoidal, square, rectangular, trapezoidal, triangular and combinations thereof. Shapes having square corners may also be replaced with rounded corners, for example, a rectangle having a square corner replaced by a rounded one may be referred to as a rounded rectangular shape.

In one embodiment cross-sectional shape of the air inhale chamber and cross-sectional shape of the air exhale chamber are independently selected from cylindrical, rectangular, rounded rectangular, trapezoidal and rounded trapezoidal. In one embodiment the cross-sectional shape is independently selected from cylindrical, rectangular, rounded rectangular, trapezoidal and rounded trapezoidal. In one embodiment the cross-sectional shape is cylindrical. In one embodiment the cross-sectional shape is rounded rectangular.

In a further embodiment, the cross-sectional shape of the air inhale chamber and/or the air exhale chamber may taper along its length from the base end to the mouthpiece end or vice versa. In one embodiment the cross-sectional shape tapers from the base end towards the mouthpiece end.

The relative size of the air inhale chamber to the air exhale chamber may be provided in different ratios depending on design requirements. The device may be designed to have the same or similar overall size compared to the prior inhaler devices for administering methoxyflurane with the added benefit of internally accommodating an air exhale chamber comprising air filtering means, such as activated carbon (AC) granules without adversely affecting the delivery of the vapor to a patient.

For example, the Green Whistle™ prior art inhaler that is currently on the market has a length of 152 mm and a diameter of 27 mm and the externally fitted AC chamber has length of 78 mm, a width of 25 mm and a height of 35 mm. In one embodiment, the dimensions of the device of the present invention which comprises an internally positioned air exhale chamber comprising an air filtering means, such as activated carbon (AC) granules, in a co-axial air inhale-exhale chamber arrangement, is of a similar dimension to the Green Whistle device.

In one embodiment the mouthpiece end optionally comprises a diluter hole. A diluter hole may function to vary the amount of vapor in the air/vapor mixture that is delivered to a patient upon inhalation. For example, when the diluter hole is partially or completely open or uncovered, the concentration of the vapor in the air/vapor mixture may be relatively diluted and when the diluter hole is closed or covered, the concentration of the vapor in the air/vapor mixture may be relatively increased.

The diluter hole may be partially or completely closed or covered by the patient simply by placement of the patient's finger partially or completely over the diluter hole when in use.

The cross-sectional shape of the mouthpiece end may be the same or different to the rest of the device. In one embodiment, the mouthpiece chamber is tapered towards the mouthpiece end. In a preferred embodiment the cross-sectional shape of the mouthpiece end is adapted to fit a conventional aerosol or nebuliser face mask.

In one embodiment the base end is an integrally formed feature of the inhaler device. In one embodiment the base end comprises a liquid inlet hole.

In one embodiment the base end comprises one or more protrusions such as lugs to assist with opening the liquid storage container.

In another embodiment the base end comprises an end cap. In one embodiment the base end and the end cap comprise a liquid inlet hole.

In one embodiment the end cap is a removable end cap. In another embodiment the end cap is an adjustable end cap such as a rotatable end cap cover. The rotatable end cap cover may be detachably fastened to rotatingly engage with the rest of the device by, for example, a screw thread arrangement, interference or press fit arrangement or a snap-fit joint arrangement.

In one embodiment the end cap comprises one or more protrusions such as lugs to assist with opening the liquid storage container.

In one embodiment the end cap comprises a wad insert. The wad insert may comprise a compressible material and a vapor impermeable film or foil to assist with providing a tight seal when the adjustable end cap is closed. Examples of compressible materials include but are not limited to polymeric foams or sponges such as LDPE. The vapor impermeable film or foil is as defined herein.

It may also be desirable to direct the site(s) of deposition of the liquid onto the passive evaporation support material and to improve its distribution once deposited. In one embodiment, the liquid inlet hole in the base end and/or end cap comprises an optional liquid inlet guide. The inlet guide may be in the form of a funnel, gutter, channel, chute, domed surface or the like. Without wishing to be bound by theory, the inlet guide may offer the advantage of assisting the distribution of the poured liquid onto and throughout the passive evaporation support material by being designed to disrupt or break the surface tension of the poured liquid as it leaves the inlet guide and/or direct the location of the liquid's initial site(s) of contact with the passive evaporation support material.

Examples of liquid storage containers which may be suitable for use in the present invention include, but are not limited to vials, bottles, ampoules or vapor impermeable sachets or packets. The liquid storage containers may be made from glass or one or more materials as described herein that are compatible with the storage of halogenated volatile liquids such as, for example, vapor impermeable films, polymers, composites, metals and combinations thereof.

In one embodiment, the liquid storage container is a capped bottle wherein the cap comprises: an end seal; a threaded arrangement adapted to rotatingly engage with a threaded neck of the bottle; and a point of weakness; wherein the point of weakness is adapted to break the end seal when the bottle is rotated relative to the cap. In one embodiment the cap is adapted to matingly engage with the base end of the inhaler device to hold the cap in place while the bottle is rotated by a user.

It is considered that the cap design and/or opening mechanism for use with an inhaler device to deliver an inhalable liquid such as methoxyflurane is new. Accordingly, in one embodiment there is provided a capped bottle for use with an inhaler device to deliver an inhalable liquid wherein the cap comprises: an end seal; a threaded arrangement adapted to rotatingly engage with a threaded neck of the bottle; and a point of weakness; and further wherein the cap is adapted to matingly engage with the inhaler device to hold the cap in place and the point of weakness is adapted to break the end seal when the bottle is rotated relative to the cap.

The point of weakness in the cap may be formed as a thinned section, such as a grooved section or similar.

To facilitate the ease of administration, in particular self-administration, the device may be pre-loaded with a storage container of the inhalable liquid.

Accordingly, in another embodiment the device further comprises a storage chamber for internally holding an inhalable liquid storage container wherein the storage chamber is adapted to deliver the inhalable liquid from the liquid storage container into the air inhale chamber and onto the passive evaporation support material.

In one embodiment, the storage chamber is movable relative to the air inhale chamber. In one embodiment the storage container is movably connected to the base end of the device.

In one embodiment, the storage chamber comprises an unopened inhalable liquid storage container in a first position wherein the storage chamber is movable to a second position to open the liquid storage container to deliver the inhalable liquid from the liquid storage container into the air inhale chamber and onto the passive evaporation support material.

The type of liquid storage container will determine how it may be opened to deliver or release the inhalable liquid onto the passive evaporation support material. For example, a vial with a screw cap lid may be opened by unscrewing the lid, a vial with a plug may be opened by unplugging i.e. by pulling out the plug or pushing it into the vial, a vial sealed with a vapor impermeable film may be opened by puncturing or piercing the film, an ampoule may be opened by snapping or crushing and vapor impermeable sachets or packets may be opened by ripping, unpeeling, pulling, perforating or tearing.

In one embodiment, the liquid storage container is selected from the group consisting of a vial or bottle (preferably a glass vial or bottle), an ampoule (preferably a glass ampoule) and a vapor impermeable sachet or packet.

In one embodiment the storage chamber delivers the inhalable liquid into the air inhale chamber by pushing, sliding or rotating the liquid storage container into an opened position.

In one embodiment the liquid storage container is selected from a vial comprising a screw cap lid and the storage chamber is adapted to deliver the inhalable liquid from the vial into the air inhale chamber and onto the passive evaporation support material by rotating the storage chamber relative to the air inhale chamber to unscrew cap lid to open the vial by moving the vial from a first position into a second position.

In one embodiment the liquid storage container is a capped bottle where the cap has an intentional point of weakness which allows the cap to fail when overtightened and the storage chamber is adapted to deliver the inhalable liquid from the capped bottle into the air inhale chamber and onto the passive evaporation support material by twisting or rotating the storage chamber relative to the air inhale chamber to break the cap along the point of structural weakness to open the bottle by moving the bottle from a first position into a second position.

In one embodiment the liquid storage container is a vial with a plug and the storage chamber is adapted to deliver the inhalable liquid from the vial into the air inhale chamber and onto the passive evaporation support material by pushing the storage chamber relative to the air inhale chamber to push the plug into the vial to open the vial by moving the vial from a first position into a second position.

In one embodiment the liquid storage container is a vial sealed with a vapor impermeable film and the storage chamber is adapted to deliver the inhalable liquid from the vial into the air inhale chamber and onto the passive evaporation support material by puncturing or piercing the film to open the vial by moving the vial from a first position into a second position.

In one embodiment the liquid storage container is an ampoule and the storage chamber is adapted to deliver the inhalable liquid from the ampoule into the air inhale chamber and onto the passive evaporation support material by rotating the storage chamber relative to the air inhale chamber to snap the ampoule to open the ampoule by moving the ampoule from a first position into a second position.

In one embodiment the liquid storage container is a vapor impermeable sachet or packet and the storage chamber is adapted to deliver the inhalable liquid from the sachet or packet into the air inhale chamber and onto the passive evaporation support material by moving the storage chamber relative to the air inhale chamber to rip, perforate or tear the sachet or packet to open the sachet or packet.

In one embodiment, the storage sachet is entirely formed from a vapor impermeable film adapted to sealingly store the halogenated volatile liquid. When the storage sachet is entirely formed from a vapor impermeable film it may be sealed by sealing an outer perimeter portion of the vapor impermeable film to itself. In another embodiment, the storage sachet is formed from a vapor impermeable film having a base portion wherein the vapor impermeable film is adapted to sealingly store the halogenated volatile liquid together with the base portion and further wherein the base portion is rigid or semi-rigid.

In one embodiment the base portion is formed from a polymer as described herein. To reduce manufacturing costs the base portion and the inhaler body may be formed from the same polymer. The base portion will typically be planar but may optionally comprise a receptacle portion for receiving the halogenated volatile liquid. When the storage sachet is formed from a vapor impermeable film having a base portion it may be sealed by sealing a perimeter edge of the base portion with an outer perimeter portion of the vapor impermeable film. Where the base portion comprises a receptacle portion, the perimeter edge of the base portion may be a lip of the receptacle. Further, the receptacle portion may form part of the inhaler device itself as further described in embodiments herein.

When the storage sachet is positioned within the inhaler device for administration of the halogenated volatile liquid to the patient, the storage sachet may be opened by removing the vapor impermeable film or a portion thereof by peeling, pulling, tearing, ripping, perforating, puncturing or piercing.

To assist opening the storage sachet by peeling, pulling, tearing or ripping, the storage sachet may optionally comprise a pull tab which may protrude through an opening in the inhaler body, whereby it can be gripped and pulled by the user to release the inhalable liquid thereby avoiding movable components of the device itself to open the storage sachet. Accordingly, in one embodiment the storage sachet comprises a pull tab adapted to open the storage sachet by peeling, pulling, tearing or ripping the vapor impermeable film. The pull tab may be made from any suitable material capable of connecting to the vapor impermeable film and withstanding the pulling or peeling forces required to open the storage sachet. The pull tab may be integrally formed and connected to the vapor impermeable film and in one embodiment the pull tab is integrally formed from the vapor impermeable film.

The pull tab may also be independently formed and connected to the vapor impermeable film and in one embodiment the pull tab is made from a different material to the vapor impermeable film.

To assist opening the storage sachet by perforating, puncturing or piercing, the sachet may engage with the inhaler body which may optionally comprise a perforating, puncturing or piercing means operable by movement of the device.

Examples of vapor impermeable films include but are not limited to polymeric films, metal foils (such as, for example, aluminium, nickel and alloys thereof) and combinations, including co-extruded polymeric films and/or foils such as laminate films, thereof. In one embodiment the vapor impermeable film is a single layer selected from a polymeric film or a metal foil. In another embodiment the vapor impermeable film is a laminate film comprising two or more layers selected from a polymeric film, a metal foil and combinations, including co-extruded polymeric films and/or foils, thereof. The laminate film may comprise a weldable layer made from a suitable weldable foil or polymeric film such as, for example, LLDPE. A weldable layer may assist with sealing the layers of a laminate together and/or sealing a vapor impermeable film comprising a weldable layer to the device. Processes suitable for welding include thermal and ultrasonic welding.

In one embodiment the polymeric film has a MVTR of less than 100 $g/m^2/24h$, preferably less than 50 $g/m^2/24h$. In one embodiment the polymeric film comprises a polymer selected from the group consisting of a polyolefin, a polymeric phthalate, a fluorinated polymer, a polyester, a nylon, a polyvinyl, a polysulfone, a natural polymer and combinations, including co-extruded polymers thereof including biaxially orientated polymers such as, for example, biaxially orientated polypropylene (BOPP). In one embodiment the polymeric film comprises a polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof.

In one embodiment the vapor impermeable film comprises PET. In another embodiment the vapor impermeable film comprises PET and a metal foil layer, preferably an aluminium foil layer. In one embodiment the vapor impermeable film comprises metalised PET (Met PET).

In one embodiment the vapor impermeable film comprises a co-extruded polymer layer adhered to a metalised PET layer adhered to an externally peelable LLDPE layer. In a further embodiment the co-extruded polymer layer is a biaxially orientated polymer, preferably BOPP. In another embodiment the vapor impermeable film comprises a layer of BOPP adhered to a metalised PET layer adhered to an externally peelable LLDPE layer.

The present device is considered to be particularly useful for administering a halogenated volatile liquid, particularly methoxyflurane for use as an analgesic. Accordingly, in one embodiment the inhalable liquid is a halogenated volatile liquid. In a further embodiment the halogenated volatile liquid is selected from the group consisting of halothane (2-bromo-2-chloro-1,1,1-trifluoroethane), sevoflurane (fluoromethyl-2,2,2-trifluoro-1-(trifluroromethyl)ethyl ether), desflurane (2-difluoromethyl-1,2,2,2-tetrafluoroethrylether), isoflurane (1-chloro-2,2,2-trifluoroethyldifluoromethyl ether), enflurane (2-chloro-1,1,2-trifluoroethyldifluoromethyl ether) and methoxyflurane (2,2-dichloro-1,1-difluoroethylmethyl ether). In a preferred embodiment, the inhalable liquid is methoxyflurane for use as an analgesic.

Suitable delivery doses of inhalable liquid for administration to a patient by the present device may be determined by reference to, for example, regulatory approved dosage amounts. Suitable delivery doses of methoxyflurane for use as an analgesic will typically be less than 15 mL and preferably less than 12 mL. In one embodiment the delivery dose is selected from the group consisting of 0.5 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL, 10.5 mL, 11 mL, 11.5 mL and 12 mL. In one embodiment the delivery dose of methoxyflurane for administration by the present device is selected from the group consisting of 1.5 mL, 3 mL and 6 mL.

The device may be made from various materials. However, suitable material(s) may be selected by considering whether they are chemically inert, stable and impervious with reference to the inhalable liquid to be stored and/or delivered. Material(s) may also be selected based on their suitability for medical device applications such as by reference to whether they meet approved standards for medical-grade human use by a regulatory authority like the FDA.

It is envisaged that the present device will be particularly useful for administering halogenated volatile liquids. Accordingly, in one embodiment, the device is made from one or more materials that are compatible with the delivery of halogenated volatile liquids to a patient, in particular methoxyflurane for use as an analgesic.

Examples of materials which may be suitable for making the present device include but are not limited to polymers (including homopolymers and heteropolymers i.e. co-polymers), composites (including nanocomposites), metals (including alloys thereof) and combinations thereof. In one embodiment, the device is made from polymers (including homopolymers and heteropolymers i.e. co-polymers), composites (including nanocomposites such as polymers in combination with clay), metals (including aluminium and alloys thereof) and combinations thereof. In a further embodiment, the device is optionally internally lined or coated with one or more material(s) selected from the group consisting polymers (including homopolymers and heteropolymers i.e. co-polymers), composites (including nanocomposites such as polymers in combination with clay), metals (including aluminium, nickel and alloys thereof), oxides (including aluminium oxides, silicon oxides), resins (including epoxyphenolic resins and ionomeric resins such as Surlyn®, trademark of DuPont), lacquers and enamels.

It is considered that one advantage of the present device is its relative simplicity and low cost to manufacture in addition to the ease of operability in terms of the minimum number of individual components or parts required for the administration of the inhalable liquid. For example, the device may be formed as a single manufactured part.

Embodiments of the device may require additional manufactured parts such as for example valves, an inlet guide, a liquid guide, an end cap such as an adjustable end cap and/or a removable end cap as described herein. Each manufactured part may be separately formed from the same or a different material. In one embodiment, the separately manufactured parts of the device are independently made from a material selected from the group consisting of a polymeric material, a metal (for example, aluminium, nickel) and a metal alloy (for example, stainless steel).

Polymers are particularly suited to large scale manufacturing of the present device and polymeric films described herein by injection moulding, blow moulding and extrusion processes. They may also be suitable for manufacturing the present device on a smaller scale by 3D printing techniques. Further, polymers may be recycled following disposal of the device.

Examples of polymers for use in making the present device and polymeric films described herein may include but are not limited to the following polymers and combinations (including co-extruded polymers) thereof: polyolefins such as polypropylene ('PP'), polyethylene ('PE') including low density ('LDPE'), linear low density ('LLDPE') and high density polyethylene ('HDPE'), biaxially orientated polypropylene ('BOPP'), 4-methylpentene, polymethylpentene, polycyclomethylpentene; polymeric phthalates such as polyethylene naphthalates ('PEN'), polyethylene terephthalate ('PET') (also known as ('PETE')), polyethylene terephthalate polyester 'PETP', polyethylene isophthalate ('PEI'), polybutylene terephthalate ('PBT'), polytrimethylene terephthalate ('PTT'), polycyclohexylenedimethylene terephthalate ('PCT'); fluorinated polymers including polymers fluorinated after manufacture (e.g. fluorination post-moulding), fluorinated ethylene-propylene, chlorotrifluoroethylene ('Kel-F'), polytetrafluoroethylene ('PTFE'); polyesters including cellulose acetate, polyoxymethylene ('POM') and polyesters containing a terephthalate ester group including co-polymers such polyethylene terephthalate glycol co-polyester ('PETG'), polycyclohexylenedimethylene terephthalate glycol modified ('PCTG') and polycyclohexylenedimethylene terephthalate/isophthalic acid ('PCTA'); nylons including amorphous nylon; polyvinyls including polyvinyl alcohol ('PVA') and ethylene vinyl alcohol ('EVOH'); polysulfones including polyethersulfone ('PES'); and natural polymers including starch, cellulose and proteins. Suitable polymers may also include polymers with a moisture vapor transmission rate ('MVTR', also known as water vapor transmission rate 'WVTR') of less than 100 g/m$^2$/24 h, preferably less than 50 g/m$^2$/24 h.

Accordingly, in one embodiment the device is made from one or more polymers wherein the device further comprises an optional internal lining or coating with one or more material(s) selected from the group consisting polymers (including homopolymers and heteropolymers (also known as co-polymers) and combinations thereof including co-extruded polymers), composites (including nanocomposites such as polymers in combination with clay), metals (including aluminium, nickel and alloys thereof), oxides (including aluminium oxides, silicon oxides), spray coatings, resins (including epoxyphenolic resins and ionomeric resins such as Surlyn®, trademark of DuPont), lacquers and enamels.

In one embodiment the polymer is selected from a polyolefin, a polymeric phthalate, a fluorinated polymer, a polyester, a nylon, a polyvinyl, a polysulfone, a natural polymer and combinations, including co-extruded polymers thereof. In one embodiment the polymer has a MVTR of less than 100 g/m$^2$/24 h, preferably less than 50 g/m$^2$/24 h. In one embodiment the polyolefin is selected from the group consisting of PP, PE, LDPE, LLDPE, HDPE, 4-methylpentene, polymethylpentene polycyclomethylpentene and combinations, including co-extruded polymers, thereof. In one embodiment the polymeric phthalate is selected from the group consisting of PEN, PET, PETP, PEI, PBT, PTT, PCT and combinations, including co-extruded polymers thereof such as BOPP. In one embodiment the fluorinated polymer is selected from Kel-F, PTFE and combinations, including co-extruded polymers thereof. In one embodiment the polyester is selected from the group consisting of cellulose acetate, POM and polyesters containing a terephthalate ester group including PETG, PCTG, PCTA and combinations, including co-extruded polymers, thereof. In one embodiment the nylon is an amorphous nylon. In one embodiment the polyvinyl is selected from PVA, EVOH and combinations, including co-extruded polymers, thereof. In one embodiment the polysulfone is PES. In one embodiment the natural polymer is selected from the group consisting of starch, cellulose, proteins and combinations, including co-extruded polymers, thereof.

In one embodiment the device is made from a single polymer selected from the group consisting of PP, PE, LDPE, LLDPE, HDPE, BOPP, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In another embodiment the device is made from two or more polymers selected from the group consisting of PP, PE, LDPE, LLDPE, HDPE, 4-methylpentene, polymethylpentene polycyclomethylpentene, PEN, PET, PETP, PEI, PBT, PTT, PCT, Kel-F, PTFE, cellulose acetate, POM, PETG, PCTG, PCTA, nylon, PVA, EVOH, starch, cellulose, proteins and combinations, including co-extruded polymers, thereof. In one embodiment, the device is made from a polymer selected from the group consisting of HDPE, PET and combinations thereof. In one embodiment the device comprises PET.

In one embodiment there is provided an inhaler device for the delivery of methoxyflurane to a patient, said device comprising:

(1) A base end comprising an end cap with a liquid inlet hole;

(2) A mouthpiece end comprising a mouthpiece chamber and optionally comprising a diluter hole;

(3) A co-axial air inhale-exhale chamber arrangement comprising:

(a) an air inhale chamber comprising a liquid inlet hole and a passive evaporation support material comprising a wicking material for receiving the methoxyflurane from a liquid storage container and delivering to the patient as a vapor upon inhalation by the patient through the mouthpiece end;

(b) an air exhale chamber comprising activated carbon granules to filter the vapor upon exhalation by the patient through the mouthpiece end and exit through the base end; and (c) a valve;

wherein the air exhale chamber is co-axially positioned internally within the air inhale chamber (or vice versa) with an optional connector.

Preferably the air exhale chamber is co-axially positioned internally within the air inhale chamber.

In a further embodiment the valve is selected from a multi-directional valve arrangement (such as a two-way valve) and/or one or more one-way valves.

In a further embodiment, when the connector is present, the connector comprises a first connector component adapted to join with a second connector component wherein the air inhale chamber comprises said first connector component and the air exhale chamber comprises the second connector component.

In another embodiment the device comprises a support means adapted to create an air gap between a surface of the passive evaporation support material and an internal surface of the air inhale chamber. In a further embodiment the support means comprises one or more ridges or ribs that run longitudinally along a length of an internal surface of the air inhale chamber.

In yet another embodiment the air inhale chamber comprises a liquid guide.

In still another embodiment the air exhale chamber comprises an exhaust port.

In another embodiment, when the air filtering substance is activated carbon granules, the device comprises a carbon dust retaining filter.

As the inhalable liquid may be self-administered by a patient using the device, the device may optionally comprise a lanyard and a point for attachment thereto for placement around the patient's wrist or neck. Accordingly, in one embodiment the device comprises a lanyard and a point for attachment thereto.

Example 1

FIG. 1 shows the prior art Green Whistle™ inhaler device (1) (Medical Developments International Limited) which is currently used in Australia for the delivery of Penthrox®/™ (methoxyflurane) as an analgesic (1.5 mL or 3 mL, storage brown glass vial container with screw cap). When required for use, the delivery dose of methoxyflurane is poured into the base end (3) of the device. After the dose is poured into the base end for delivery onto the evaporative means (not shown), the methoxyflurane evaporates so that the patient can self-administer the analgesic by inhaling the air/vapor mix through the mouthpiece (2). Provided that the patient continues to breathe through the mouthpiece, any exhaled air/vapor mix will exit the device via the externally fitted chamber containing activated carbon 'AC-chamber' (4).

Example 2

Figure 2:
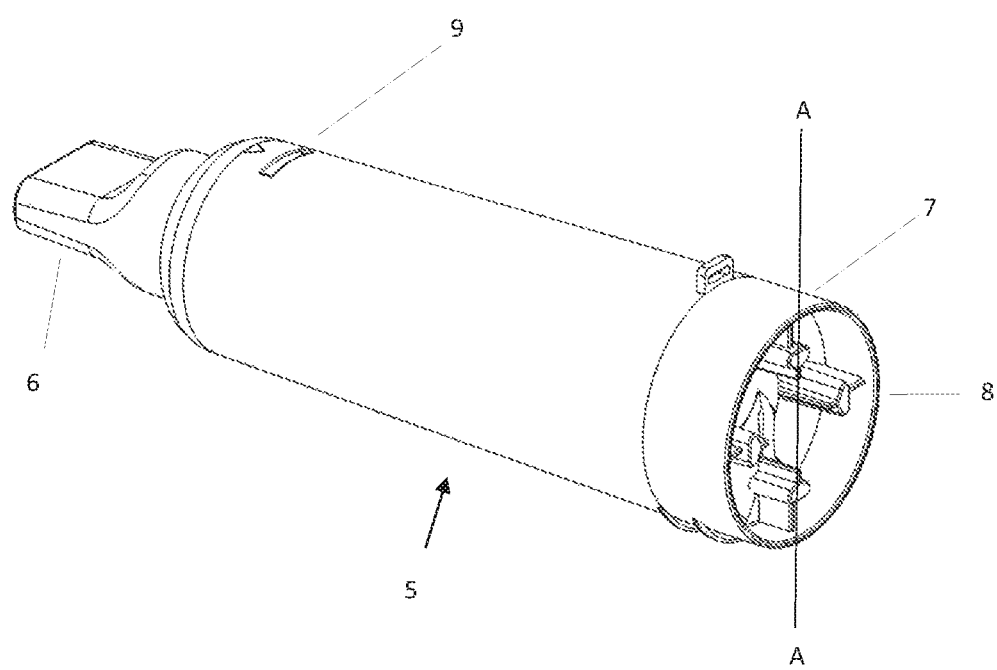
FIG. 2 shows an inhaler device according to an embodiment of the invention having a co-axial air inhale-exhale chamber arrangement with cylindrical cross-sectional air inhale and air exhale chambers.
Figure 3A:
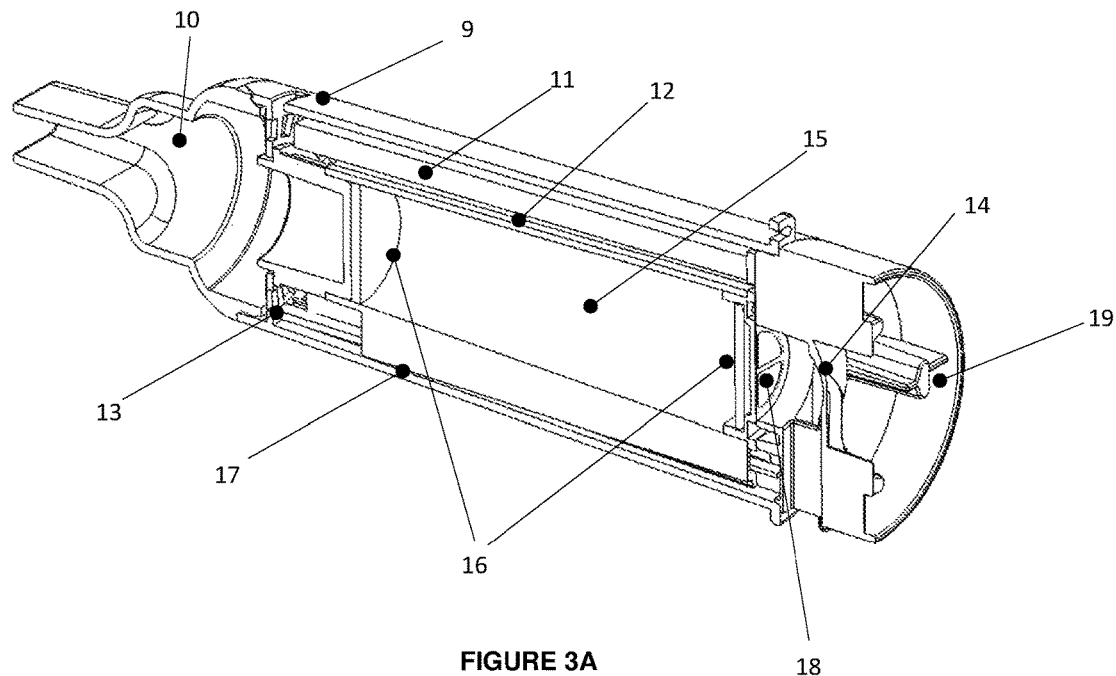
FIG. 3 shows a cross-sectional cut-away view of the device of FIG. 2 along line A-A with (FIG. 3A) and without (FIG. 3B) the passive evaporative support material in the air inhale chamber.
Figure 3B:
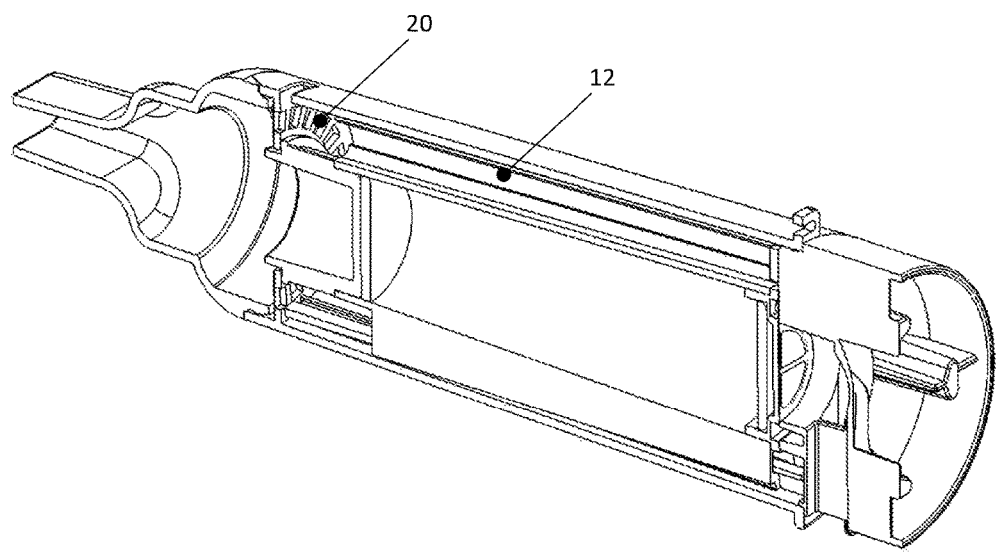
Figure 4:
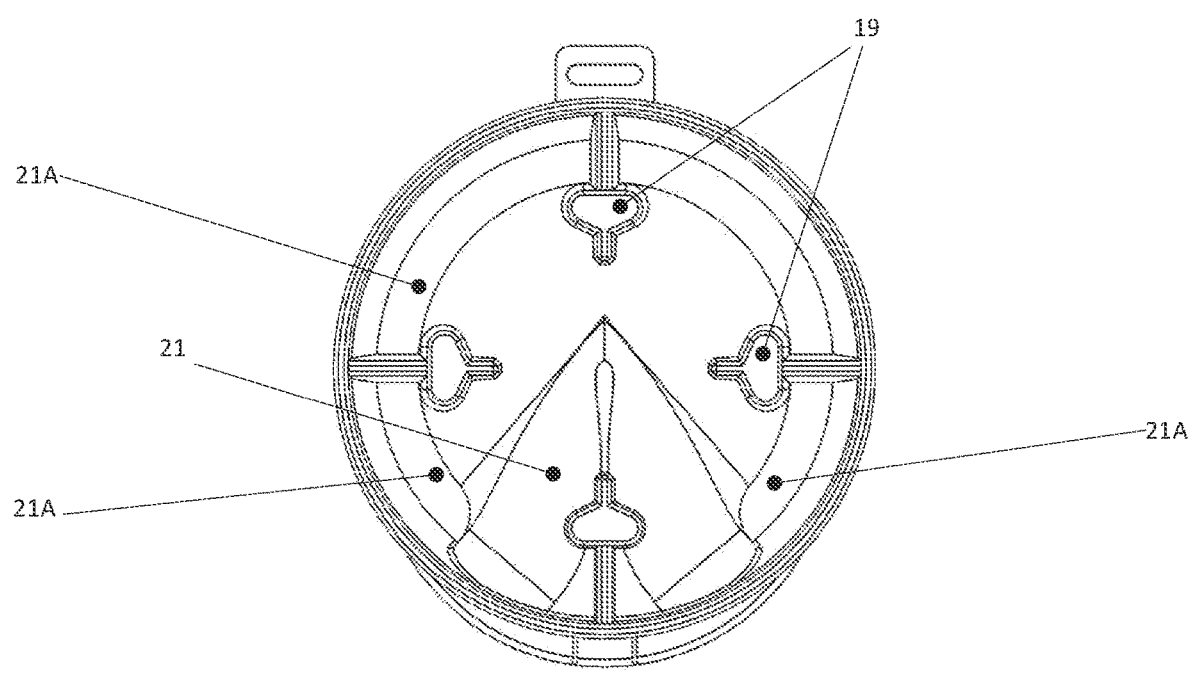
FIG. 4 shows a rear view of the end cap of the device of FIG. 2.
Figure 5:
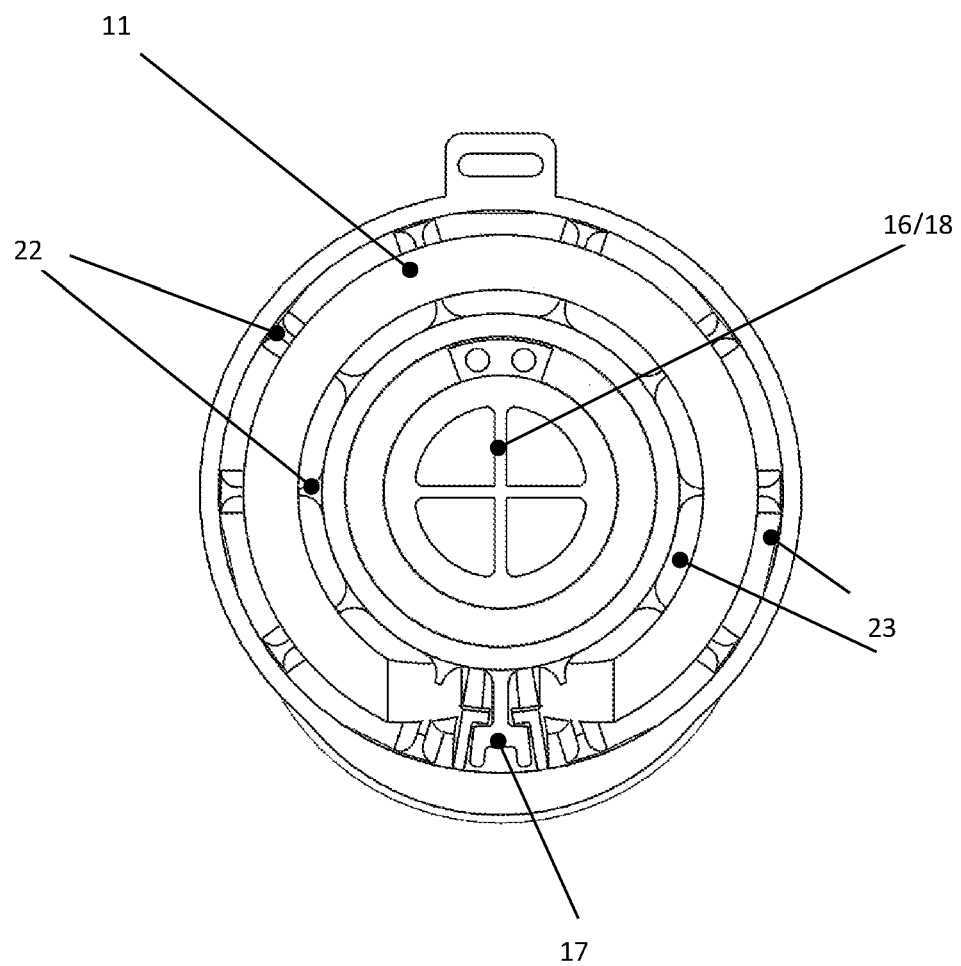
FIG. 5 shows a rear view of the device of FIG. 2 with the end cap removed to illustrate an embodiment of the co-axial air inhale-exhale chamber arrangement where the air exhale chamber comprising activated carbon ('AC') granules is internally positioned within the air inhale chamber and also illustrating selected optional features of the air exhale chamber including a carbon dust retaining filter and an exhaust port.
Figure 6:
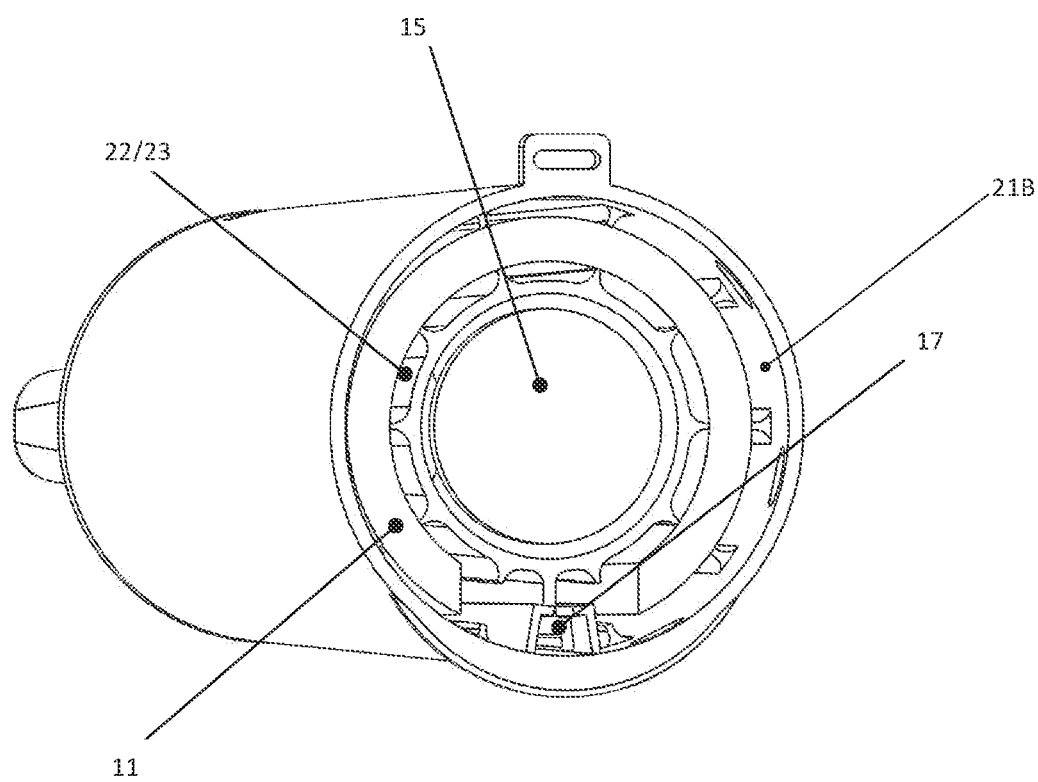
FIG. 6 shows a perspective rear view of the device of FIG. 2 with the end cap removed to illustrate an embodiment of the co-axial air inhale-exhale chamber arrangement without the AC granules and also illustrated the selected optional features shown in FIG. 5.

FIG. 2 shows an inhaler device (5) according to an embodiment of the invention with a cylindrical cross-sectional shape along its length. The device comprises a mouthpiece end (6) and base end (7) with an end cap (8) and optional diluter hole (9). A cross-sectional cut-away view of the device along line A-A is shown in FIG. 3A to illustrate some of the internal features of the device such as a mouthpiece chamber (10), passive evaporation support material (11) in the air inhale chamber (12), a one-way annular valve (13) positioned between the air inhale chamber and the mouthpiece chamber, one-way flap exhaust valve (14) in the base end of the air exhale chamber (15), carbon dust retaining filters (16), a connector in the form of a keyway mechanism (17), an exhaust port (18) and end cap lugs (19). FIG. 3B is the same presentation as 3A but with the passive evaporation support material in the air inhale chamber (12) removed to better illustrate the liquid guide in the form of a castellation arrangement with radial guide fingers (20). FIG. 4 presents a rear view of the end cap having lugs (19) to assist with removal of a cap from a capped bottle comprising the inhalable liquid, such as methoxyflurane, and pouring into the air inhale chamber onto the passive evaporation support material via a liquid inlet guide (21), end cap liquid inlet (21A) and air inhale chamber liquid inlet (21B). Another rear view of the based end of the device is presented in FIG. 5 with the end cap removed to better illustrate some of the internal features including: the keyway mechanism (17); carbon dust retaining filter (16) and exhaust port (18); and passive evaporation support material (11) partially wrapped around the external circumference of the air exhale chamber and positioned in the air inhale chamber between support means in the form of ridges or ribs (22) that run longitudinally along a length of the internal surfaces of the air inhale chamber to create air gaps (23) through which the inhaled air and vapor mixture can pass through the air inhale chamber and into the mouthpiece chamber for delivery to a patient. FIG. 6 presents an alternative perspective rear view of FIG. 5 to illustrate the co-axial arrangement with an empty (i.e. without the activated carbon granules present) air exhale chamber (15) having a cylindrical cross-sectional shape along its length positioned internally by keyway mechanism (17) within the air inhale chamber (also having a cylindrical cross-sectional shape along its length) comprising the passive evaporation support material (11) located between the ridges/ribs (22) and air gaps (23) arrangement.

Example 3

Figure 7A:
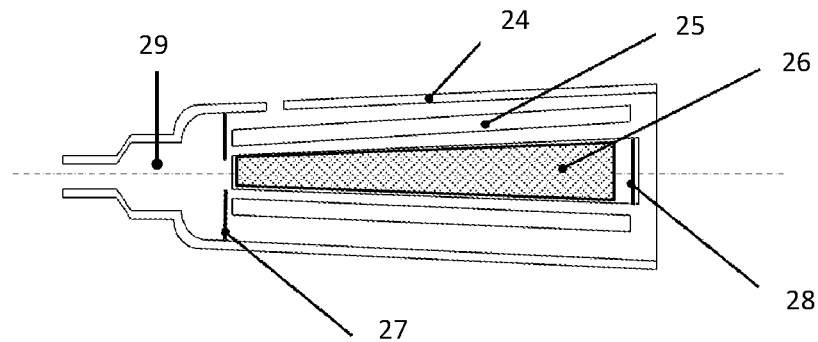
FIG. 7 shows a longitudinal cut-away view an inhaler device according to an embodiment of the invention having a co-axial air inhale-exhale chamber arrangement with tapering cross-sectional air inhale and air exhale chambers (FIG. 7A) and the direction of air flow through the device and opening of the valve arrangement as illustrated by the arrows upon inhalation (FIG. 7B) and exhalation (FIG. 7C) by a patient.
Figure 7B:
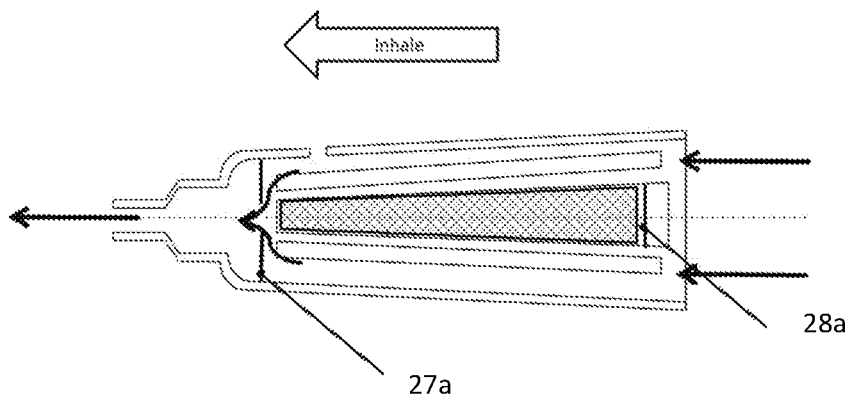
Figure 7C:
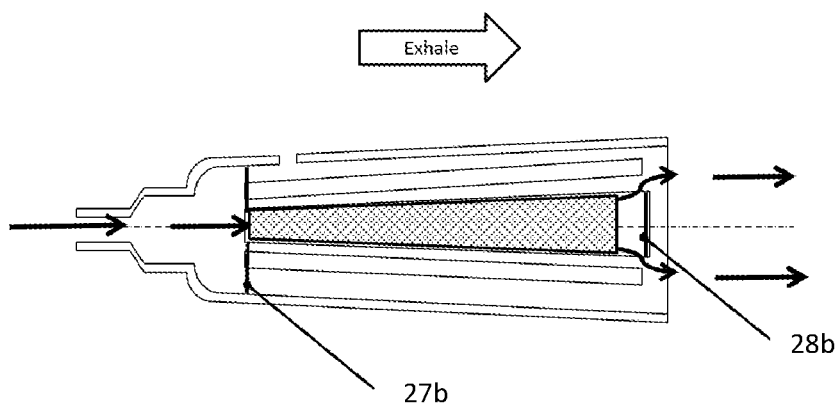

FIG. 7 shows a longitudinal cut-away view of an inhaler device according to an embodiment of the invention with a cross-sectional shape tapering towards the mouthpiece end along its length. As shown in FIG. 7A, the device comprises an air inhale chamber (24), a passive evaporation support material (25) wrapping around the external circumference of an air exhale chamber comprising activated carbon (AC) granules (26) and two valves, namely a one-way air inhale valve (27) between the air inhale chamber (24) and mouthpiece chamber (29) and a one-way air exhale valve (28) in the base end of the air exhale chamber (26) to exhaust the exhaled air flow from the mouthpiece chamber (29). Upon inhalation of a patient through the mouthpiece chamber (29) the air inhale valve opens (27a) and the air exhale valve closes (28a) to allow the air to flow into the device in the direction of the arrows shown to deliver vapor to the patient. Upon exhalation by a patient through the mouthpiece chamber the reverse occurs, that is, the air inhale valve closes (27b) and the air exhale valve opens (28b) to allow the exhaled air to flow out of the device in the direction of the arrows shown though the air exhale chamber comprising the air filtering substance to remove any exhaled vapor.

Example 4

Figure 8A:
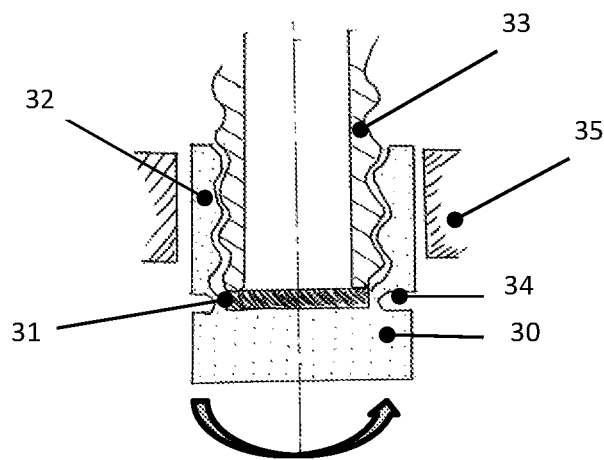
FIG. 8 shows a capped liquid container according to an embodiment of the invention for use in an inhaler device.
Figure 8B:
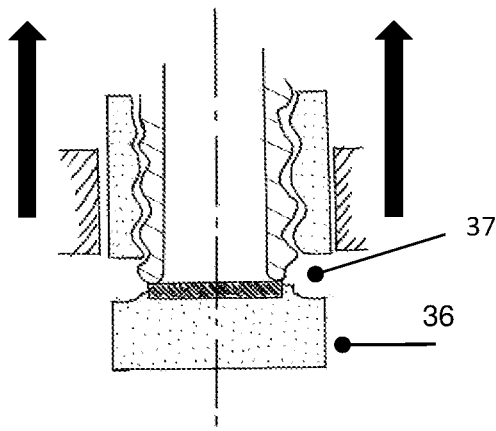
Figure 8C:
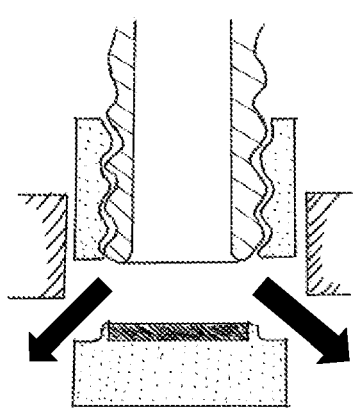

Figure shows the features of a capped liquid container, more specifically a cap for a capped bottle according to an embodiment of the invention for use in an inhaler device. Shown in FIG. 8A is the cap (30) which has an end seal (31), a threaded arrangement (32) adapted to rotatingly engage with the threaded neck of the bottle (33) and a point of weakness being a thinned section in the form of a groove (34). The cap engages with an inhaler device (35) where it is held in place i.e. the threaded arrangement (32) is prevented from rotating when the exposed end of the cap is rotated in the direction of the arrow shown e.g. clockwise. As shown in FIG. 8B, as the bottle is rotated relative to the exposed end of the cap (36) causes the cap to tighten and break the at the point of weakness (37) resulting in threaded arrangement being moved along the threaded neck of the bottle in the direction of the arrows shown until it is pushed up into the inhaler to a point where it gets pressed into and locks it up such that the user is unable to turn it any more. Rotation of the bottle by the user in the opposite direction e.g. anticlockwise, and pulling to remove the bottle and threaded arrangement out of the inhaler breaks the seal causing the liquid contents of the bottle to be released in the direction of the arrows shown in FIG. 8C.

Example 5

The ability of an inhaler device to delivery methoxyflurane may be tested using a breath simulator system such as a pulmonary waveform generator system.

The delivery of methoxyflurane (% concentration) by the Green Whistle device with the external AC chamber attached and a Prototype device (FIG. 7) according to an embodiment of the invention was measured using a pulmonary waveform generator system. The Prototype device was manufactured as a rapid prototype using a HDPE equivalent material.

Both devices were tested as follows. The pulmonary waveform generator was set to "Adult" flow conditions (14 breaths per minute) and the concentration logging software and Datex Sensor commenced. For each test, methoxyflurane (3 mL) was poured into the device so that the polypropylene wick was pre-loaded with the methoxyflurane to be delivered and the mouthpiece end of the device then inserted into the opening of the pulmonary waveform generator. Concentration logging was commenced for the first minute for the first breaths concentration and then for the next 20 minutes for steady state testing.

Figure 9:
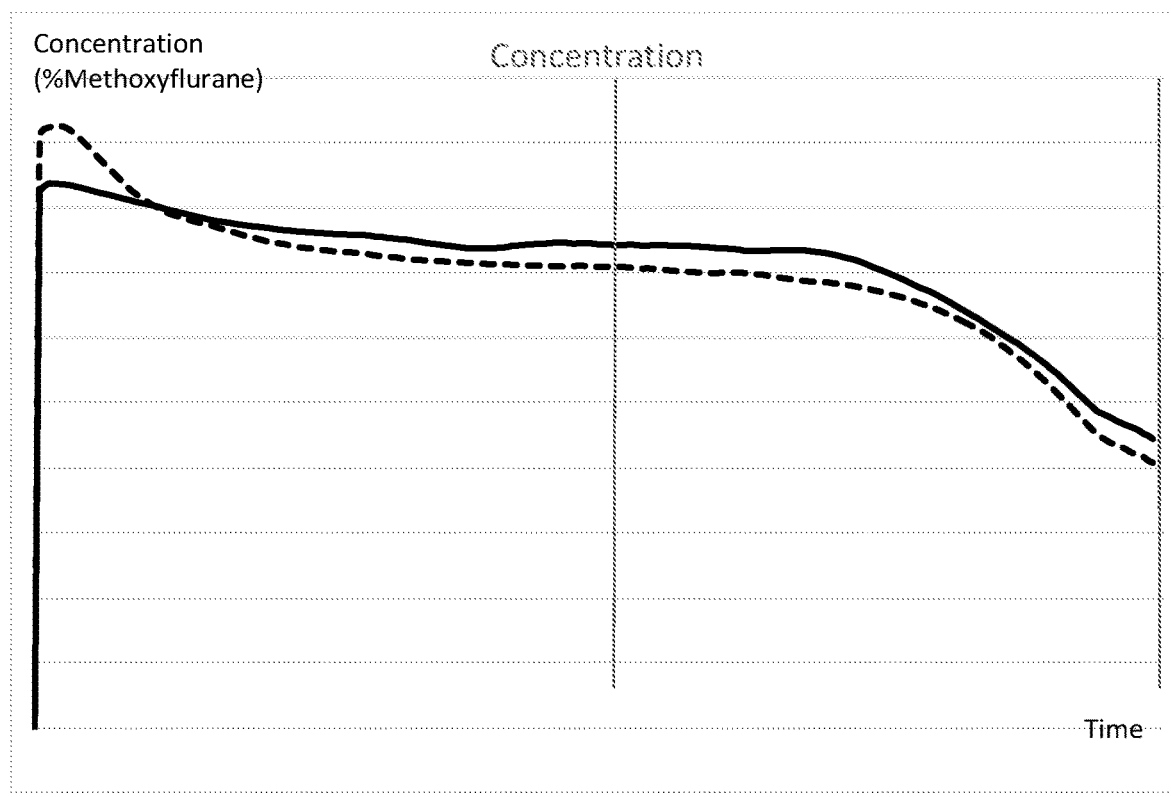
FIG. 9 shows the comparative concentrations of methoxyflurane delivered by a device (FIG. 7) according to an embodiment of the invention and the prior art Green Whistle inhaler (FIG. 1).

The results are presented in FIG. 9. In both cases, the devices delivered methoxyflurane at the same or similar levels to each other and to acceptable levels for patient use for example by reference to the regulatory approved levels for the Green Whistle device.

Throughout this specification and the claims which follow, unless the context requires otherwise, the word "comprise" and variations thereof such as "comprises" and "comprising", will be understood to imply the inclusion of a stated integer or step or group of integers or steps but not to the exclusion of any other integer or step or group of integers or steps.

The reference in this specification to any prior publication or information derived from it, or to any matter which is known is not and should not be taken as an acknowledgement or admission or any form of suggestion that prior publication, or information derived from it, or known matter, forms part of the common general knowledge in the field of endeavour to which this specification relates.

The invention claimed is:

1. An inhaler device for the delivery of an inhalable liquid to a patient, said device comprising:
    a base end;
    a mouthpiece end comprising a mouthpiece chamber;
    a co-axial air inhale-exhale chamber arrangement comprising:
        (a) an air inhale chamber comprising a liquid inlet hole and a passive evaporation support material for receiving the inhalable liquid from a liquid storage container and delivering the inhalable liquid to the patient as a vapor upon inhalation by the patient through the mouthpiece end; and
        (b) an air exhale chamber comprising an air filter to filter the vapor upon exhalation by the patient through the mouthpiece end and exit through the base end;
        wherein the air exhale chamber is co-axially positioned internally within the air inhale chamber;
        a first one-way valve located between the mouthpiece chamber and the air inhale chamber, the first one way valve configured to enable inhalation air to pass through the air inhale chamber into the mouthpiece chamber and prevent exhalation air passing into the air inhale chamber; and
        a second one-way valve located at the base end, the second one-way valve configured to enable exhalation air to pass out of the air exhale chamber and prevent inhalation air passing through the air exhale chamber,
        wherein the air inhale chamber further comprises a diluter hole.

2. The inhaler device according to claim 1 wherein the co-axial air inhale-exhale chamber arrangement comprises a connector to co-axially position the air exhale chamber internally within the air inhale chamber.

3. The inhaler device according to claim 2 wherein the connector is integrally formed with the air inhale and air exhale chambers.

4. The inhaler device according to claim 2 wherein the connector comprises a first connector component adapted to join with a second connector component wherein the air inhale chamber comprises the first connector component and the air exhale chamber comprises the second connector component.

5. The inhaler device according to claim 1 wherein the air exhale chamber is co-axially positioned internally within the air inhale chamber by virtue of the passive evaporation support material.

6. The inhaler device according to claim 1 wherein the device has an external cross-sectional shape along its length selected from the group consisting of circular, semi-circular, elliptical, semi-elliptical, oval, ovoidal, square, rectangular, trapezoidal, triangular and combinations thereof.

7. The inhaler device according to claim 6 wherein the external cross-sectional shape of the device tapers along its length from the base end to the mouthpiece end or vice versa.

8. The inhaler device according to claim 1 wherein the air inhale chamber and air exhale chamber have a cross-sectional shape along their lengths that is the same.

9. The inhaler device according to claim 8 wherein the cross-sectional shape of at least one of the air inhale chamber or the air exhale chamber tapers along its length from the base end to the mouthpiece end or vice versa.

10. The inhaler device according to claim 1 wherein a cross-sectional shape of the air inhale chamber and a cross-sectional shape of the air exhale chamber are each selected from the group consisting of circular, semi-circular, elliptical, semi-elliptical, oval, ovoidal, square, rectangular, trapezoidal, triangular and combinations thereof.

11. The inhaler device according to claim 1 wherein the mouthpiece end comprises the mouthpiece chamber configured such that the vapor is inhaled into the mouthpiece chamber from the air inhale chamber and exhaled into the mouthpiece chamber and exited through the base end via the air exhale chamber.

12. The inhaler device according to claim 1 wherein the air inhale chamber comprises a liquid guide to direct the liquid to make contact with the passive evaporation support material.

13. The inhaler device according to claim 1 wherein the air exhale chamber is co-axially positioned internally within the air inhale chamber and the passive evaporation support material partially or completely surrounds an external surface of the air exhale chamber.

14. The inhaler device according to claim 13 wherein the passive evaporation support material is positioned in the air inhale chamber by a support structure, and wherein the support structure is adapted to create an air gap between a surface of the passive evaporation support material and an internal surface of the air inhale chamber.

15. The inhaler device according to claim 14 wherein the support structure comprises one or more ridges or ribs that run longitudinally along a length of an internal surface of the air inhale chamber.

16. The inhaler device according to claim 14 wherein the support structure is adapted to expose one surface area of the passive evaporation support material to a flow of inhaled air.

17. The inhaler device according to claim 14 wherein the support structure is adapted to expose two surface areas of the passive evaporation support material to a flow of inhaled air.

18. The inhaler device according to claim 1 wherein the passive evaporation support material is a polypropylene wicking felt.

19. The inhaler device according to claim 1 wherein the air exhale chamber comprises an air filter comprising activated carbon to filter the vapor upon exhalation by the patient in the co-axial air inhale-exhale chamber arrangement.

20. The inhaler device according to claim 1 wherein the base end comprises an end cap.

21. The inhaler device according to claim 20 wherein the end cap comprises an end cap liquid inlet hole and an end cap liquid inlet guide.

22. The inhaler device according to claim 20 wherein the end cap comprises one or more protrusions to assist with opening the liquid storage container.

23. The inhaler device according to claim 1 wherein the device contains methoxyflurane as the inhalable liquid.

24. The inhaler device according to claim 1 wherein the device is configured to deliver methoxyflurane as the inhalable liquid in a delivery dose of up to 15 mL.

25. The inhaler device according to claim 1 wherein the device is manufactured from a material selected from the group consisting of polymers, composites, metals and combinations thereof.

26. The inhaler device according to claim 1 wherein the device is manufactured from one or more polymers and further comprises an internal lining or coating of one or more materials selected from the group consisting of polymers including homopolymers, heteropolymers or combinations thereof including co-extruded polymers; polymer composites including nanocomposites; metals or alloys thereof; oxides including aluminium oxides; silicon oxides; spray coatings; resins including epoxyphenolic resins and ionomeric resins; lacquers; and enamels.

27. The inhaler device according to claim 1 wherein the inhaler device is manufactured from one or more polymers selected from the group consisting of a polyolefin, a polymeric phthalate, a fluorinated polymer, a polyester, a nylon, a polyvinyl, a polysulfone, a natural polymer and combinations, including co-extruded polymers thereof.

28. The inhaler device according to claim 1 wherein the device is manufactured from one or more polymers selected from the group consisting of high-density polyethylene (HDPE), polyethylene terephthalate (PET) and combinations thereof.

29. The inhaler device according to claim 28 wherein the device is manufactured from PET.

30. The inhaler device according to claim 1 wherein the mouthpiece end is tapered towards a mouthpiece hole.

31. An inhaler device for the delivery of methoxyflurane to a patient, said device comprising:
  a base end comprising an end cap with a liquid inlet hole;
  a mouthpiece end comprising a mouthpiece chamber; and
  a co-axial air inhale-exhale chamber arrangement comprising:
    (a) an air inhale chamber comprising a liquid inlet hole and a passive evaporation support material comprising a wicking material for receiving the methoxyflurane from a liquid storage container and delivering the methoxyflurane to the patient as a vapor upon inhalation by the patient through the mouthpiece end;
    (b) an air exhale chamber comprising activated carbon granules to filter the vapor upon exhalation by the patient through the mouthpiece end and exit through the base end;
  wherein the air exhale chamber is co-axially positioned internally within the air inhale chamber;
  a first one-way valve located between the mouthpiece chamber and the air inhale chamber, the first one way valve configured to enable inhalation air to pass through the air inhale chamber into the mouthpiece chamber and prevent exhalation air passing into the air inhale chamber; and
  a second one-way valve located between the end cap and the air exhale chamber, the second one-way valve configured to enable exhalation air to pass out of the mouthpiece chamber through the air exhale chamber and prevent inhalation air passing through the air exhale chamber,
  wherein the inhale chamber further comprises a diluter hole.

* * * * *